(12) United States Patent
Webster

(10) Patent No.: US 11,679,253 B2
(45) Date of Patent: Jun. 20, 2023

(54) WEARABLE MEDICAL DEVICE WITH INTEGRATED BLOOD OXYGEN SATURATION LEVEL DEVICE

(71) Applicant: West Affum Holdings, Grand Cayman (KY)

(72) Inventor: Brian D. Webster, Mercer Island, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 77 days.

(21) Appl. No.: 17/133,939

(22) Filed: Dec. 24, 2020

(65) Prior Publication Data

US 2021/0252277 A1 Aug. 19, 2021

Related U.S. Application Data

(60) Provisional application No. 62/977,363, filed on Feb. 16, 2020.

(51) Int. Cl.
*A61N 1/39* (2006.01)
*A61N 1/04* (2006.01)
*A61N 1/365* (2006.01)

(52) U.S. Cl.
CPC .......... *A61N 1/046* (2013.01); *A61N 1/0484* (2013.01); *A61N 1/36514* (2013.01); *A61N 1/3904* (2017.08); *A61N 1/3925* (2013.01); *A61N 1/3993* (2013.01)

(58) Field of Classification Search
CPC .............................. A61N 1/046; A61N 1/3904
USPC ............................................................ 607/5
See application file for complete search history.

(56) References Cited

U.S. PATENT DOCUMENTS

| 3,724,355 | A | 4/1973 | Unger |
| 4,583,524 | A | 4/1986 | Hutchins |
| 4,619,265 | A | 10/1986 | Morgan et al. |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Bornn et al. |
| 5,353,793 | A | 10/1994 | Bornn |
| RE34,800 | E | 11/1994 | Hutchins |
| 5,394,892 | A | 3/1995 | Kenny |

(Continued)

FOREIGN PATENT DOCUMENTS

| EP | 3380189 B1 | 10/2018 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Nicole F Lavert

(57) ABSTRACT

Technologies and implementations for a wearable medical device (WMD). The technologies and implementations facilitate incorporating a blood oxygen saturation level device with the WMD. Additionally, the technologies and implementations include wearable cardioverter device (WCD) incorporating a blood oxygen saturation level device.

20 Claims, 12 Drawing Sheets

(56) References Cited

U.S. PATENT DOCUMENTS

| | | |
|---|---|---|
| 5,405,362 A | 4/1995 | Kramer et al. |
| 5,474,574 A | 12/1995 | Payne et al. |
| 5,618,208 A | 4/1997 | Crouse et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 9,878,171 B2 | 1/2018 | Kaib |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0067514 A1* | 3/2016 | Sullivan ............... A61B 5/0205 607/6 |
| 2016/0082277 A1 | 3/2016 | Foshee, Jr. et al. |
| 2017/0143977 A1* | 5/2017 | Kaib .................... A61N 1/0456 |
| 2017/0182330 A1* | 6/2017 | Schneider ............. G16H 20/40 |
| 2017/0266456 A1* | 9/2017 | Piha .................... A61N 1/0496 |
| 2018/0272147 A1* | 9/2018 | Freeman ................ G16H 50/30 |
| 2019/0344090 A1* | 11/2019 | Sullivan ............... A61B 5/0816 |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Cado, et al., "Encircling Overlapping Multipulse Shock Waveforms for Transthoracic Defibrillation," JACC Journals, Dec. 1998, vol. 32 Issue 7, p. 2065-2071.

* cited by examiner

1000 A computer program product

1002 A signal bearing medium 1004 at least one of machine readable non-transitory medium having stored therein instructions that, when executed by one or more processors, operatively enable a health related data correlation module (HRDCM) to:

receive, at a processor, an indication of a first health related data from a first healthcare device;

receive, at the processor, an indication of a second health related data from a second healthcare device;

correlate, by the processor, the indication of the first health related data with the second health related data;

storing, at a storage medium, the correlated indications of the first health related data and the second health related data; and determine, by the processor, an identity of a person based, at least in part, on the stored correlated indications..

| 1006 a computer-readable medium | 1008 a recordable medium | 1010 a communications medium |

Figure 10

WEARABLE MEDICAL DEVICE WITH INTEGRATED BLOOD OXYGEN SATURATION LEVEL DEVICE

RELATED APPLICATION

This application claims benefit of priority to U.S. Provisional Patent Application Ser. No. 62/977,363, filed on Feb. 16, 2020, titled WCD SYSTEM WITH GARMENT-INTEGRATED PULSE OXIMETER SENSOR, which is incorporated herein by reference in its entirety for all purposes.

INFORMATION

Unless otherwise indicated herein, the approaches described in this section are not prior art to the claims in this application and are not admitted to be prior art by inclusion in this section.

Technology has contributed to improvements in healthcare. Some examples include healthcare related devices that may be mobile and personal. Mobile and personal healthcare devices may include Wearable Medical Devices (WMDs). Some WMDs may include medical devices that facilitate monitoring of various health related activities of a person. For example, a WMD may include a medical device that may be used to monitor a person's heart activity. The heart activity monitored by the WMD may be in the form of electrical signals (i.e., electrocardiogram or ECG). The WMD may be in a form factor capable of being worn by a person, whose heart activity is to be monitored. Monitoring of a person's ECG may facilitate intervention of heart related issues.

An example of a WMD, which may be used to monitor and facilitate intervention of a person's heart activity, may be a cardioverter defibrillator type medical device (e.g., wearable cardioverter defibrillator or WCD). Some examples of WCDs may include garment or some sort of support structure that a person may wear having electronic components and electrodes configured to facilitate monitoring the person's heart activity and to facilitate providing an electrical shock to the person's heart when treatment is necessary.

In addition to monitoring a person's heart, monitoring oxygen in a person's blood may help facilitate to determine the person's health. An example of monitoring the oxygen in a person's blood may be monitoring blood oxygen saturation levels. Monitoring the blood oxygen saturation levels may help facilitate monitoring of different health related conditions (e.g., vital signs including the heart rhythm, respiration, etc.). For example, blood oxygen saturation levels may affect various organ function such as, but not limited to, brain and heart. For example, low levels of blood oxygen saturation levels may lead to heart issues including cardiac arrest. Accordingly, monitoring blood oxygen saturation levels may help facilitate detection of a variety of health related issues.

Accordingly, health care devices having a variety of monitoring devices may be capable of addressing a variety of health related issues. The variety of monitoring devices may complement each other and may provide a more comprehensive indication of a person's health. These monitoring devices may be included in a WMD.

All subject matter discussed in this section of this document is not necessarily prior art and may not be presumed to be prior art simply because it is presented in this section. Plus, any reference to any prior art in this description is not and should not be taken as an acknowledgement or any form of suggestion that such prior art forms parts of the common general knowledge in any art in any country. Along these lines, any recognition of problems in the prior art are discussed in this section or associated with such subject matter should not be treated as prior art, unless expressly stated to be prior art. Rather, the discussion of any subject matter in this section should be treated as part of the approach taken towards the particular problem by the inventor(s). This approach in and of itself may also be inventive. Accordingly, the foregoing summary is illustrative only and not intended to be in any way limiting. In addition to the illustrative aspects, embodiments, and features described above, further aspects, embodiments, and features will become apparent by reference to the drawings and the following detailed description.

SUMMARY

Described herein are various illustrative apparatus for an improved wearable medical device (WMD). Example apparatus may include wearable cardioverter defibrillator (WCD) having a pulse oximetry sensor that may be incorporated with a garment and may be configured to facilitate easy access to the pulse oximetry sensor. In some examples, a WCD may include a pulse oximetry sensor, which may be removably attached. In other examples, a WCD may include a pulse oximeter sensor integrated with a garment. In some more examples, a pulse oximetry sensor may be communicatively coupled to a WCD monitor configured to receive power from and/or provide pulse oximetry output signals to the monitor for processing the output signals into SpO2 measurements. In some embodiments, the monitor can analyze the SpO2 measurements along with other sensed patient physiological parameters to make a shock decision and/or determine the patient's health status and/or trends.

The present disclosure also describes a method of manufacturing an improved a wearable medical device (WMD). The method may include disposing one or more electronic modules within clothing. The one or more electronic modules may have electronic components configured to facilitate operation of the clothing as a WMD. Additionally, the method may include integrating the one or more electronic modules with the clothing to facilitate accommodation of the electronic components.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 10 illustrates an example computer program product arranged, in accordance with at least some embodiments described herein;

DETAILED DESCRIPTION

Figure 1:
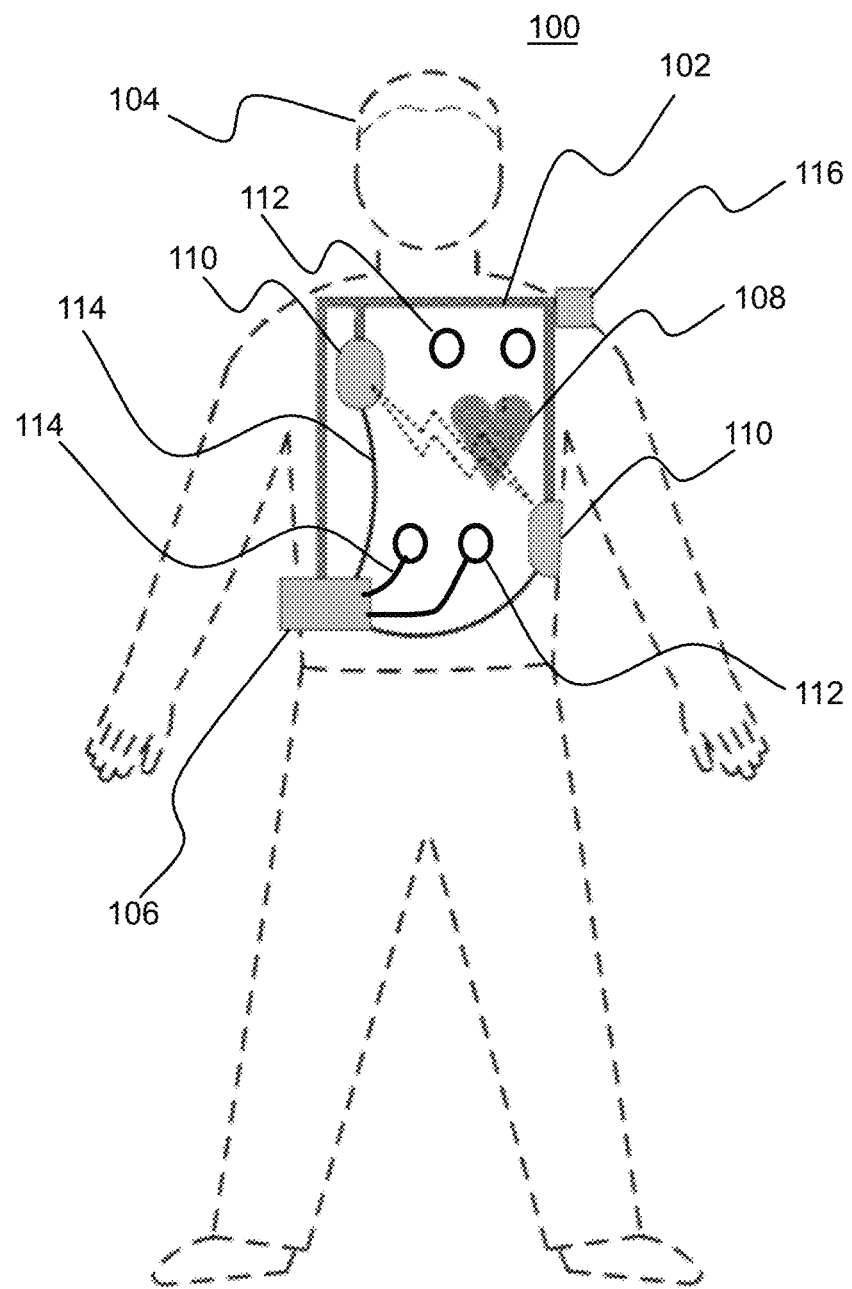
FIG. 1 illustrates a wearable medical device (WMD), in accordance with various embodiments.

The following description sets forth various examples along with specific details to provide a thorough understanding of claimed subject matter. It will be understood by those skilled in the art after review and understanding of the present disclosure, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to apparatus, systems, and methods related to a wearable cardioverter defibrillator (WCD) having a blood oxygen saturation level measurement sensor.

A wearable medical device (WMD) may be used to facilitate monitoring and treatment of various medical conditions of a person. In order to facilitate monitoring and treatment of medical conditions of a person, a WMD may be worn by the person. In order to help facilitate the wearing of the WMD, the WMD that may be included in a support structure configured to be worn by the person, where the support structure may include various components of the WMD. An example of a WMD that may facilitate monitoring and treatment of a person may include a WMD configured to facilitate monitoring and treatment of potential issues with a person's heart (i.e., the person may have a health condition, where the electrical control system of the heart may malfunction, which may cause the heart to beat irregularly or not at all). Commonly, these types of WMDs may include a defibrillator device.

Briefly, the above problem with the rate of the heartbeat may be generally referred to as arrhythmia. Arrhythmia may be caused by many factors, but in general, arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to arrhythmia of some kind. Some arrhythmias may lead to a condition known as sudden cardiac arrest (SCA). In an SCA condition, the heart may fail to pump blood effectively, and as a result, death may occur.

An example type of arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amounts of blood or may not pump blood at all, which may eventually lead to death. Another type of arrhythmia, which may be associated with SCA, may be a condition known as ventricular tachycardia (VT).

Turning back WMDs, an electronic device may be utilized to help treat VF by defibrillating the heart. An example of this type of electronic device may be a defibrillator. A defibrillator may be capable of monitoring the electrical signals of the person's heart, and if necessary, administer treatment to the heart in the form of an electric shock. The defibrillator may monitor the electrical signals and provide the electric shock to the heart externally (i.e., through the surface of a body) via accessories commonly known as electrodes. The defibrillator may be in the form of a cardioverter defibrillator. As alluded to above, the cardioverter defibrillator may be included in a support structure configured to be worn by a person. (e.g., wearable cardioverter defibrillator or WCD), which may help facilitate monitoring the electrical activities of the person's heart and providing the electric shock to the heart in the VF condition. As a result, the WCD may help prevent Sudden Cardiac Death (SCD). The WCD may have a number of electrodes to facilitate monitoring of the electrical signals of the heart (e.g., rhythm of the heart) and a couple of electrodes to administer the electric shock as treatment. As part of the monitoring (e.g., arrhythmia detection), the WCD may be configured to receive an electrocardiogram (ECG) signal from the number of electrodes (e.g., 5 ECG electrodes) on the skin of the person. In accordance with various embodiments of the present disclosure, along with the monitoring of the person's heart, the person's blood oxygen saturation level may be monitored by including a blood oxygen saturation level sensor in the support structure.

Before turning to the figures, a non-limiting example configurations and utilization of the various embodiments of the present disclosure is described. In the non-limiting example, a wearable medical device (WMD) may be utilized to facilitate monitoring and treatment of a person, which may be a wearable cardioverter defibrillator (WCD). As the name of the defibrillator indicates, the WCD may be included in a wearable support structure (e.g., garment). This wearable garment, including the WCD, may be in wide variety of forms such as, but not limited to, vests, shirts, undergarments, t-shirts, etc.

As described above, the WCD may include a number electrodes to facilitate monitoring of electrical signals from the person's heart and to facilitate an electric shock for the defibrillation process. Additionally, the WCD may include one or more electronic modules having many of the electronic components to facilitate monitoring and/or treatment of the heart (hereon, WCD monitor). The WCD monitor and the number of electrodes may facilitate the monitoring the activities of the heart and the administration of the treatment of the heart (e.g., an electric shock for defibrillation, cardioversion and/or pacing). Accordingly, the number of electrodes may be disposed on the garment proximate to the person's heart and/or close to or on the skin of the person. In accordance with the present disclosure, the WCD monitor may be disposed within and integrated with the garment resulting as a self-contained WCD.

The WCD monitor may comprise of various electronic components to facilitate operation of the WCD. For example, the WCD monitor may include a power supply such as, but not limited to, a battery to provide a defibrillator electrical shock to the person via the electrodes. Along with the battery, the WCD monitor may include one or more capacitors as part of a discharge circuit for the shock. Additionally, the WCD monitor may include a user interface such as, but not limited to, a physical button (e.g., response buttons), graphical user interface (e.g., display, interactive and non-interactive), audible interface (e.g., indication sounds), etc. The operation and coordination of the electronic components may be facilitated by a processor included in the WCD monitor being communicatively coupled to the various electronic components to facilitate operation of the WCD. It should be appreciated after review of this disclosure that the above example components are just a few examples, and accordingly, electronic components of a WCD monitor may include a wide variety of electronic components to facilitate operation of the WCD. Additionally, some of details of the WCD monitor will be described below.

Continuing with the non-limiting example of a WCD, the garment of the WCD may include blood oxygen saturation level sensors in accordance with various embodiments. The blood oxygen saturation level sensors may be implemented in a variety of methodologies such as, but not limited to, measurement of arterial oxygen saturation ($SaO_2$) levels. Additionally, the $SaO_2$ levels may be approximated by measurement of peripheral oxygen saturation ($SpO_2$) levels, which may be measured using a pulse oximeter device. The sensors of the pulse oximeter device may be integrated with the garment of the WCD to facilitate utilization of the measurements of the blood oxygen saturation levels by the WCD.

In a non-limiting scenario of utilization of the disclosure, a person may be wearing a WCD (i.e., the garment). A pulse oximeter sensor may be integrated with the garment. A WCD monitor may periodically indicate to the person wearing the garment to use the pulse oximeter sensor to measure the person's blood oxygen saturation level. The pulse oximeter sensor may be integrated into a portion of the garment (e.g., an over the shoulder strap). For example, the pulse oximeter sensor may be attached along a left shoulder strap allowing for the person to use their right hand finger for the pulse oximeter measurement by placing the finger on the pulse oximeter sensor. In one example, the pulse oximeter sensor may be discretely integrated with the garment by having the various components of the pulse oximeter sensor recessed into the strap having a cover over the space configured to accommodate the finger. When prompted by WCD monitor, the person may simply insert a finger into the space underneath the cover to activate the pulse oximeter sensor to take a measurement.

In one example, the pulse oximeter sensor may be included as part of a self-contained pulse oximeter device. The self-contained pulse oximeter device may include various electronic components to measure the blood oxygen saturation level (e.g., sensor) and display the measurements on a display of the pulse oximeter device. In another example, the pulse oximeter sensor may be communicatively coupled to the WCD monitor and transmit the data from the sensor to the WCD monitor (e.g., a processor included in the WCD monitor) to be processed with the measurement being displayed on a display of the WCD monitor. It may be appreciated that in the self-contained example above, the pulse oximeter device may include its own power supply, processor, etc. In the communicatively coupled example above, the pulse oximeter sensor may utilize the various electronic components of the WCD monitor such as, but not limited to, a power supply, a processor, a communication medium (e.g., wireless communication medium), a storage medium, etc. Alternatively, a pulse oximeter device may be a hybrid of self-contained and communicatively coupled with the WCD monitor. For example, the hybrid pulse oximeter device may include a sensor, a processor, and a display but may utilize the power supply of the WCD monitor.

Continuing with the non-limiting example scenario, the WCD monitor may determine that there may be an issue with the person's heart (e.g., a low heart rate) via the received ECG signals from the electrodes. The WCD monitor may prompt the person to utilize the pulse oximeter sensor via an interface such as, but not limited to, a display and/or an audio notification. The measurements from the pulse oximeter sensor may be transmitted to the WCD monitor. The WCD monitor may analyze the measurements from the pulse oximeter device and the ECG received signals to determine whether treatment should be administered (e.g., a shock to the heart). For this example, if the WCD monitor determines that the person's blood oxygen saturation level is within acceptable parameters, the WCD monitor may not administer the treatment (i.e., the electric shock).

Continuing with the above example, the determined issue by the WCD monitor may be detection of VF or a sustained VT, which would commonly result in the delivery of an electric shock. However, if the person responds to the provided prompt by utilizing the pulse oximeter sensor (i.e., placing the finger on the pulse oximeter sensor), the WCD monitor may terminate the shock process because the person being able to respond to the prompt may indicate that the person is not experiencing VF or VT (e.g., false indications). Accordingly, the determination of the treatment may be confirmed by analyzing a number of health related measurements (i.e., vital signs of heart rhythm and blood oxygen saturation levels) providing a more accurate information of the person's physiological parameters.

While measurements may include the status of the person's health at the time of the measurements, the measurements may include a trend as well. For example, measurements of the person's health received and analyzed at one point in time may indicate a first status of the person's health, and subsequently, measurements of the person's health received and analyzed at a second point in time may indicate a second status of the person's health. Comparing the first status and the second status may indicate a deterioration of the person's health (e.g., a negative change in the measurements). Alternatively, the first status and the second status may indicate an improvement of the person's health (e.g., a positive change in the measurements). Accordingly, increased measurements regarding a person's health (e.g., vital signs of heart rhythm and blood oxygen saturation levels) may increase accuracy of the treatment.

As will be described in detail, because the WCD monitor and the pulse oximeter sensor may be included in the garment, both the WCD monitor and the pulse oximeter sensor may be modular (i.e., the WCD monitor and the pulse oximeter sensor may be removeable). However, there may be examples, where the pulse oximeter sensor may be included in the garment in a substantially permanent manner (i.e., not be removeable).

It is contemplated within the present disclosure that in addition to increased accuracy of the treatment of a person, increased measurements regarding the person's health (e.g., vital signs of heart rhythm and blood oxygen saturation levels) may facilitate determination of a health characteristics of the person. For example, as the person wears the WCD for long periods of time, including various other health measuring devices (e.g., pulse oximeter), the various measured health indications of the person may be correlated. The correlated health indications may be processed to determine person's activities, which in turn may facilitate identifying the person through their activities and habits. As will be described, gathering measurements of a person for a prolonged period of time may provide information about the activities of the person and may lead to identifying the person. In turn, the WCD may be personalized for the person.

It should be appreciated after review of this disclosure that the above non-limiting examples facilitate utilization of a blood oxygen saturation level sensor with a WCD, where the blood oxygen saturation level sensor and the WCD may be integrated with a support structure. This integration may facilitate an increase in information of the health of a person through increased measurements such as, but not limited to, a person's ECG and a person's blood oxygen saturation level. Additionally, the increased information may facilitate identification of the person providing a more personal health monitoring system.

Turning now to FIG. 1, FIG. 1 illustrates a wearable medical device (WMD), in accordance with various embodiments. In FIG. 1, a WMD may be configured to facilitate monitoring and treatment of a person's heart such as, but not limited to, a wearable cardioverter defibrillator (WCD) 100. The WCD 100 may be included in a support structure (hereon, garment 102), which may be configured to be worn by a person 104. The WCD may include various electronic components to facilitate the functionality of the WCD as a heart monitoring and defibrillator device. The various electronic components may be illustrated as a WCD module (hereon, a WCD monitor 106). The WCD 100 may include two therapy electrodes configured to defibrillate a person's heart 108, defibrillator electrodes 110 and a number of monitoring electrodes 112 configured to detect and measure the person's electrical heart activity (e.g., electrocardiogram or ECG). As shown, the monitoring electrodes 112 and the defibrillator electrodes 110 may be located proximate to the person's heart 108 and chest area. The monitoring electrodes 112 and the defibrillator electrodes may be communicatively coupled to the WCD monitor 106 via a number of electrical leads 114. Additionally, shown in FIG. 1, the garment 102 may include a monitoring device separate from the WCD monitor 106. The separate monitoring device may be a blood oxygen saturation level device having a sensor to measure the blood oxygen saturation level (hereon, a pulse oximeter device 116). Accordingly, the WCD 100 may include measurements of the blood oxygen saturation level, which may facilitate increase in accuracy of determining the health of the person, as previously described.

In one example, the pulse oximeter device 116 may be communicatively coupled to the WCD monitor 106. In this example, the pulse oximeter device 116 may have a sensor for measurements without the need for various other electronic components. Accordingly, the pulse oximeter device 116 may transmit blood oxygen saturation level measurements to the WCD monitor 106 to be processed and analyzed (e.g., utilize the processors and various electronic components of the WCD monitor 106 including its power supply). The processed and analyzed measurements may be provided to the person 104 via a display (not shown), which may be included in the WCD monitor.

In another example, the pulse oximeter device may be substantially self-contained (i.e., have various electronic components to function as a pulse oximeter device including a power supply). In this example, the pulse oximeter device 116 may process and analyze the person's blood oxygen saturation level measurements and provide the results to the person 104 via a display, which may be included as part of the pulse oximeter device 116.

In yet another example, the pulse oximeter device 116 and the WCD monitor 106 may be communicatively coupled, where the pulse oximeter device 116 may process and analyze the person's blood oxygen saturation level measurements. The processed and analyzed measurements may be transmitted to the WCD monitor 106 to be displayed on the display on the WCD monitor 106.

In yet a further example, the pulse oximeter device 116 and the WCD monitor 106 may be communicatively coupled to facilitate a hybrid self-contained pulse oximeter device 116. In this example, the pulse oximeter device 116 may configured to utilize one or more electronic components included in the WCD monitor 106. As a result, the WCD 100 may include a blood oxygen saturation level device (the pulse oximeter device 116) to facilitate increased physiological parameters of the person's health contributing to an increase in accuracy of treatment (e.g., defibrillation) of the person 104.

As described with respect to the non-limiting scenarios, in one example, the WCD monitor 106 may provide a prompt to the person 104 to measure a blood oxygen saturation level by utilizing the pulse oximeter device 116. Accordingly, the person 104 may insert a finger (in this case, the person's right hand finger) into the pulse oximeter 116. These prompts may be determined by various factors such as, but not limited to, periodic schedule, detection of a low heart rate via the monitor electrodes 112, a predetermined change in the respiration rate, which may be determined by the WCD monitor, etc.

In another example, the WCD monitor may be configured to issue a prompt to the person 104 to measure a blood oxygen saturation level by utilizing the pulse oximeter device 116 when the WCD monitor 106 detects VF or a sustained VT. In this example, the WCD monitor 106 may be preparing to deliver a defibrillating electric shock to the person 104 via the defibrillator electrodes 110. However, if the person 104 responds by using the pulse oximeter device 116, the WCD monitor 106 may terminate the shock process because it may be unlikely that the person 104 would be able to respond if the person 104 is experiencing VF or VT. Accordingly, this example may be utilized as part of the WCD monitor alarm system.

It should be appreciated that the pulse oximeter device 116 may be communicatively coupled to the WCD monitor 106 physically or wirelessly. Additionally, even though the WCD monitor 106 may be shown as a single module, the various components of the WCD may be dispersed throughout the garment 102. Further, the garment 102 may be a variety of support structures such as, but not limited to clothing such as, but not limited to, a vest, a jacket, a t-shirt, a dress shirt, a belt, a blouse, a coat, and any combination thereof. Accordingly, the claimed subject matter is not limited in these respects.

Figure 2A:
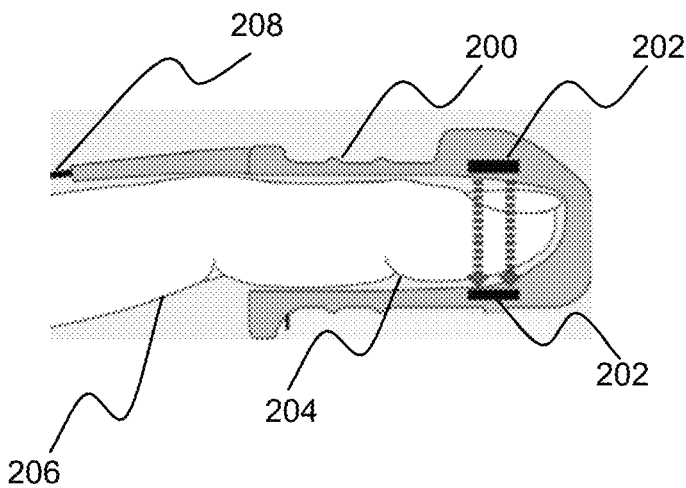
FIGS. 2A, 2B, and 2C illustrate examples of blood oxygen saturation level devices, which may be utilized with the various embodiments.
Figure 2B:
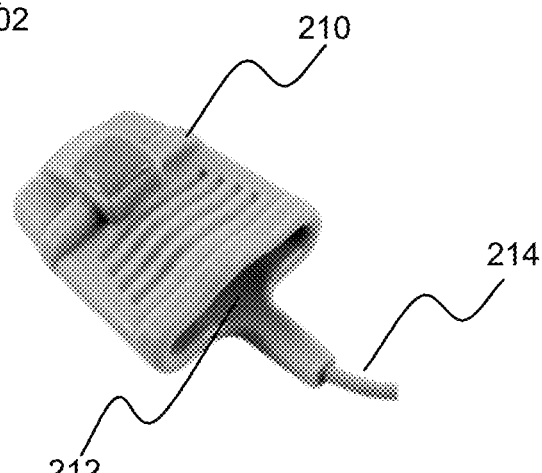
Figure 2C:
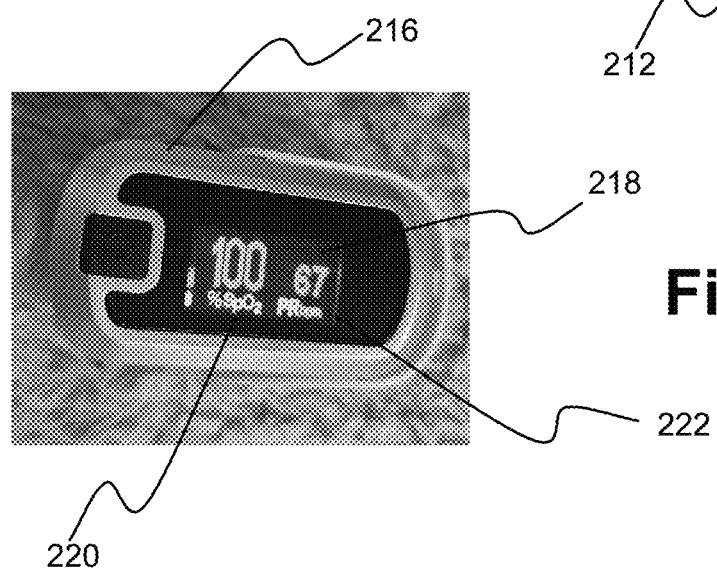

FIGS. 2A, 2B, and 2C illustrate examples of blood oxygen saturation level devices, which may be utilized with the various embodiments. Shown in FIG. 2A is a cross section of a pulse oximeter 200. The pulse oximeter 200 may include sensors 202 inside a space 204 configured to accommodate a finger 206. Additionally, the pulse oximeter 200 may include a physical cable 208 to be communicatively coupled to a WCD monitor. It should be noted that the sensors 202, which may be utilized to measure the blood oxygen saturation level, may be included as part of the pulse oximeter 200, but however, the sensors 202 may be separately included in a support structure, in accordance with various embodiments.

Turning now to FIG. 2B, a pulse oximeter 210 may be in the form of a pouch type, which may be made of a relatively soft and/or resilient material. In FIG. 2B, a finger may be placed into a pouch type space 212, where a fingertip may be placed on the sensors 202 (shown in FIG. 2A). In the example shown, the pulse oximeter 210 may be communicatively coupled to a WCD monitor via a physical electrical connection 214.

FIG. 2C illustrates a pulse oximeter 216, which may be of a self-contained type device. In FIG. 2C, the pulse oximeter 216 may include various electronic components to measure, process, and/or analyze the blood oxygen saturation level of the person, including being configured to display the results on a display 218. As shown in FIG. 2C, the blood oxygen saturation level device may display the person's blood oxygen saturation level 220 along with the person's heart rate 222 in beats per minute.

In FIGS. 2A-C, the pulse oximeters 200, 210, and 216 may be included in a support structure (e.g., garment/clothing) along with a WCD. These pulse oximeters 200, 210, and 216 may be configured to be attachable to and detachable from the support structure (e.g., via hook and loop fasteners, snap fasteners, magnets, etc.). Additionally, the pulse oximeters 200, 210, and 216 may be integrated into the support structure. For example, the pulse oximeter 210 of FIG. 2B may recessed into the support structure and have a cover (not shown) over the pouch type space 212. When the cover is lifted to place the finger 206, the sensors 202 (both shown in FIG. 2A) may be activated. The pulse oximeters 200, 210, and 216 may be in a sleep mode until activated. Accordingly, in one example, activating of the pulse oximeters 200, 210, and 216 may occur when placement of the finger 206 on the sensor 202 (both shown in FIG. 2A) is detected resulting in measurements being taken. That is, the pulse oximeters 200, 210, and 216 may be include an ON-OFF switch that may be actuated into an ON position when the person inserts the finger 206 into pulse oximeters 200, 210, and 216 (place on the sensors 202) and may be actuated into an OFF position when the person removes the finger 206 from the into pulse oximeters 200, 210, and 216 (removed from the sensors 202).

Briefly turning to FIG. 2C, the pulse oximeter 216 may be communicatively coupled with the WCD monitor 106 wirelessly utilizing wireless protocols such as but not limited to, Bluetooth® type, IEEE 802 based, mesh local area network (LAN) type (e.g., ZigBee, Bluetooth Low Energy, Z-Wave, 6LoWPAN, Thread, etc.), and any combination thereof. The self-contained pulse oximeter 216 may include various electronic components to facilitate a wide variety of communication capabilities.

In FIGS. 2A and 2B, the pulse oximeters 200 and 210 may have been described as being communicatively coupled to a WCD monitor via physical electrical connection. However, it should be appreciated that the pulse oximeters 200 and 210 may be communicatively coupled to a separate device such as, but not limited to, a separate pulse oximeter device, which may be self-contained. The self-contained pulse oximeter device may be communicatively coupled to a WCD monitor via a variety of manners such as, but not limited to, physical electrical connection, wireless connection, and any combination thereof.

Here again, it should be noted that even though FIGS. 2A-C have been described as pulse oximeters 200, 210, and 216, the sensors 202 may be utilized separately from the structures of the pulse oximeters 200, 210, and 216. Accordingly, use of the term pulse oximeter and pulse oximeter sensor may be interchangeable.

Figure 3A:
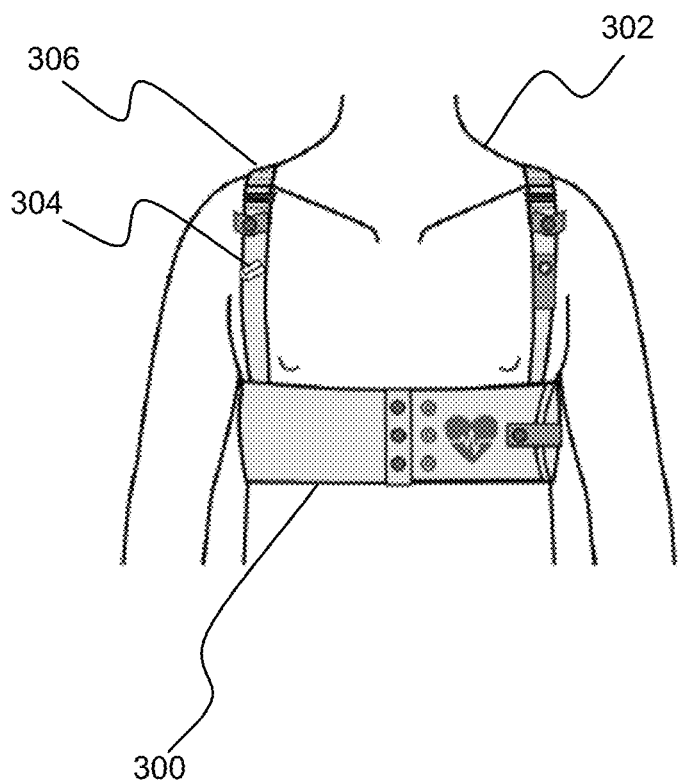
FIGS. 3A and 3B illustrate some examples of support structures, in accordance with various embodiments.
Figure 3B:
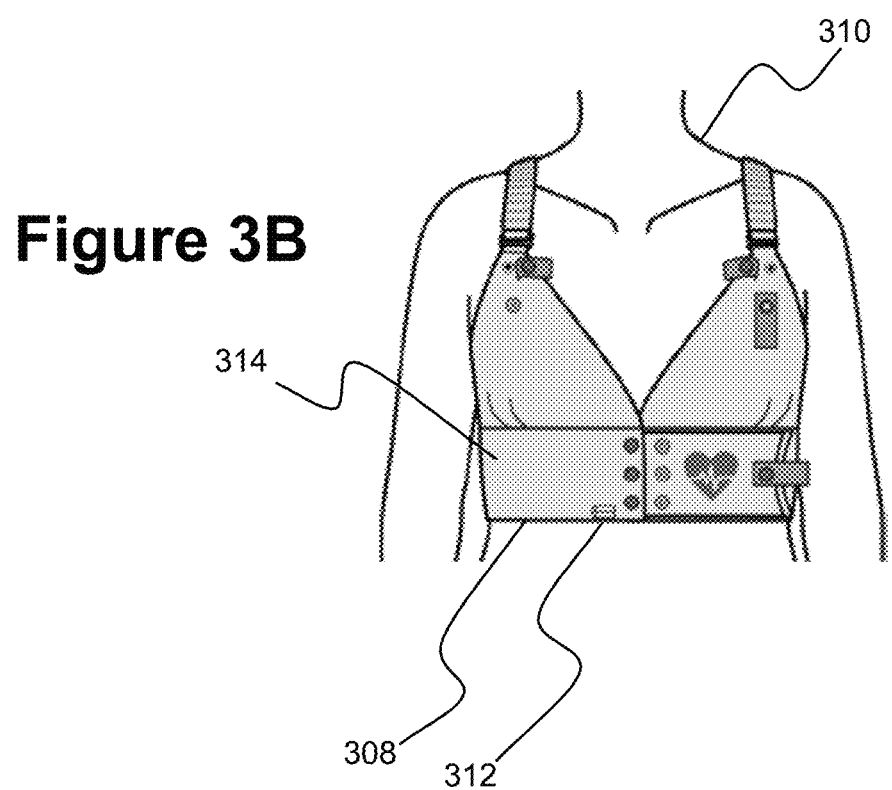

FIGS. 3A and 3B illustrate some examples of support structures, in accordance with various embodiments. In FIG. 3A, a first example of a support structure 300 may be configured to be worn by a person 302. The support structure 300 may include a WCD, where the various components of a WCD including a WCD monitor (see FIG. 1) may be integrated into the support structure 300 (i.e., discreetly hidden from view). Additionally, shown in FIG. 3A, the support structure 300 may include a pulse oximeter 304. The pulse oximeter 304 may be integrated into the support structure 300, in accordance with various embodiments. As shown, the pulse oximeter 304 may be located and positioned on the support structure 300 to facilitate ease of utilization (i.e., placing a finger into the pulse oximeter with minimal adjustment of the person's clothing). In this example, the pulse oximeter 304 may be located on an over the shoulder strap 306. Having the pulse oximeter 304 located on the shoulder strap 306 may position the pulse oximeter 304 proximate to the person's neck area, where the opening of the pulse oximeter 304 may be directed towards the person's neck. As a result, the person 302 may easily place their left hand finger into a space configured to accommodate of the pulse oximeter device 304 discretely underneath or close to a collar area. For example, if the person 302 was wearing some clothing with a collar, the person 302 may discreetly place their fingertip into the pulse oximeter 304.

In FIG. 3B, a second example of a support structure 308 may be configured to be worn by a person 310. As with FIG. 3A, the support structure 308 may include a WCD, where the various components of a WCD including a WCD monitor (see FIG. 1) may be integrated into the support structure 308 (i.e., discreetly hidden from view). Additionally, shown in FIG. 3B, the support structure 308 may include a pulse oximeter 312. As with FIG. 3A, in FIG. 3B, the pulse oximeter device 312 may be located and positioned on the support structure 308 to facilitate ease of utilization (i.e., placing a finger into the pulse oximeter device with minimal adjustment of the person's clothing). In this example, the pulse oximeter 312 may be located on a portion of the support structure configured to encompass a torso portion of the person 310 (e.g., belt portion 314). Having the pulse oximeter 312 located on the belt portion 314 may position the pulse oximeter 312 in a location, where the person 310 may be able to place their right hand finger into a space configured to accommodate of the pulse oximeter 312 discretely underneath their clothing. For example, the person 310 may be able to lift the bottom portion of their article of clothing and discretely place their fingertip into the pulse oximeter 312.

It should be appreciated that a variety of support structures may be utilized to include a WCD and a pulse oximeter. For example, a support structure may be in the form of a garment that may be worn under a person's clothing. In this example, a pulse oximeter may be located proximate to the end of a sleeve facilitating easy access to the space configured to accommodate a finger in the pulse oximeter (i.e., the sensors). As a result, a person may easily insert their finger into the pulse oximeter device located at the end of the sleeve.

In one example, the pulse oximeter may be attached to a support structure by a portion of a cabling to facilitate adjustment of position of the pulse oximeter by a person to facilitate insertion of the person's finger into a pulse oximeter device comfortably. For example, the length of a person's arm may make certain locations of the pulse oximeter more comfortable than other locations. The adjustable cabling (e.g., changeable length) may facilitate continued communicative coupling of the pulse oximeter with a WCD monitor.

In another example, the support structure may include a flap, cover, or other protective cover over a pulse oximeter (e.g., the sensors). The cover may be configured to be slid or lifted out of the way to expose the opening configured to accommodate a finger. In this example, when the cover is moved out of the way, the pulse oximeter may be activated to facilitate the sensors to take measurements.

In accordance with various embodiments, the above examples provide a support structure having a pulse oximeter device that may be utilized while a person may be wearing the support structure (i.e., garment). This integration may increase the utilization of the pulse oximeter device because there may be less likelihood of forgetting the device, misplacing the device, and damaging the device. Additionally, this integration reduces the likelihood that a person may need to connect a separate pulse oximeter to a defibrillator of some kind prior to use, which may add an additional step in measuring the blood oxygen saturation level and may be undesirably less discrete when performed in public. Additionally, it should be appreciated that having one medical device (e.g., a blood oxygen saturation level device) integrated with a support structure (e.g., a garment), where the support structure includes a second medical device may facilitate increased accuracy of measurements (e.g., vital signs) and increased accuracy of treatment.

Figure 4:
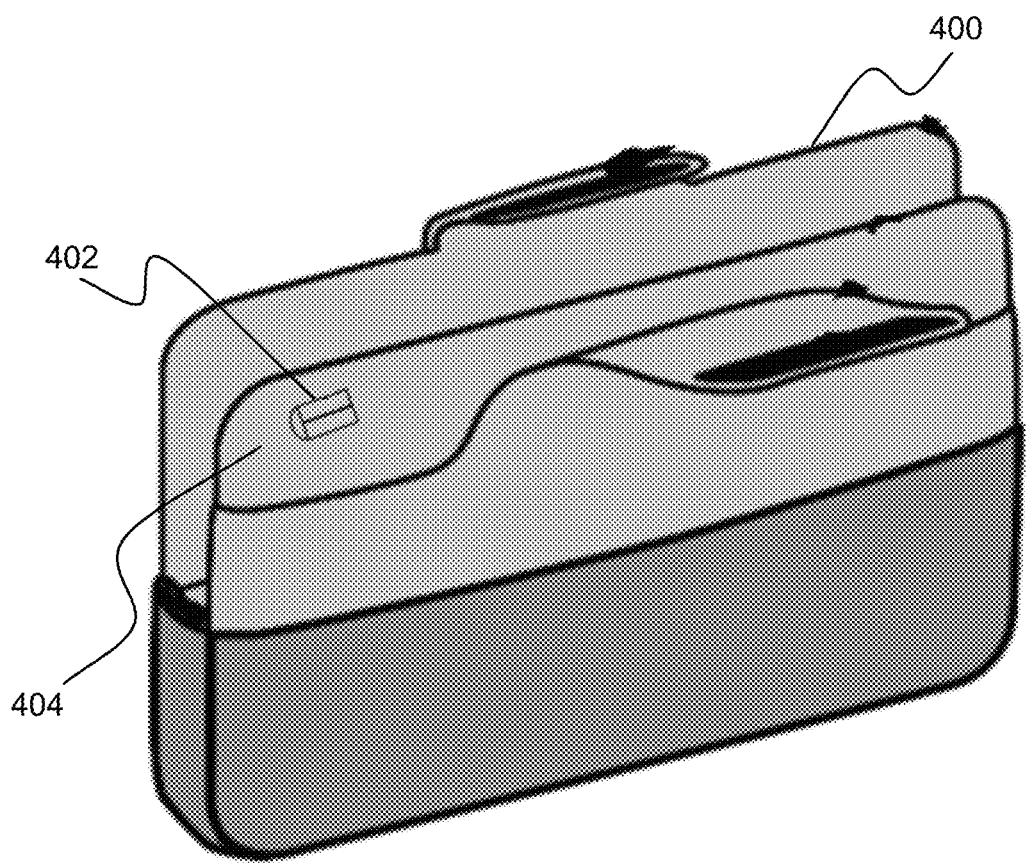
FIG. 4 illustrates integration of a blood oxygen saturation level device integrated with a mobile structure, in accordance with some embodiments.

FIG. 4 illustrates integration of a blood oxygen saturation level device integrated with a mobile structure, in accordance with some embodiments. In FIG. 4, a carry pack 400 may include a pulse oximeter 402. The carry pack 400 may be configured to hold a WCD monitor (not show), where the carry pack 400 may be worn by a person by being attachable (e.g., clipped) to a belt worn by the person or carried using shoulder straps. The pulse oximeter 402 may be disposed on an outer surface 404 of the carry pack 400. The pulse oximeter 402 may be communicatively coupled to the WCD monitor within the carry pack 400. The person may simply insert a finger into the pulse oximeter 402 on the outer surface 404 of the carry pack 400 and take a blood oxygen saturation level measurement. The measurement may be transmitted to the WCD monitor to be processed and analyzed.

In one example, when a defibrillator is no longer needed a WCD system may be reconfigurable to remove defibrillator component but retain the ECG and pulse oximeter functionality. For example, even though a person may have received an implanted defibrillator, medical personnel may want to continue monitoring the person. Accordingly, in this example, a support structure may include ECG monitoring functionality (e.g., electrodes and monitoring functionality) and blood oxygen saturation level functionality (e.g., pulse oximeter).

Figure 5:
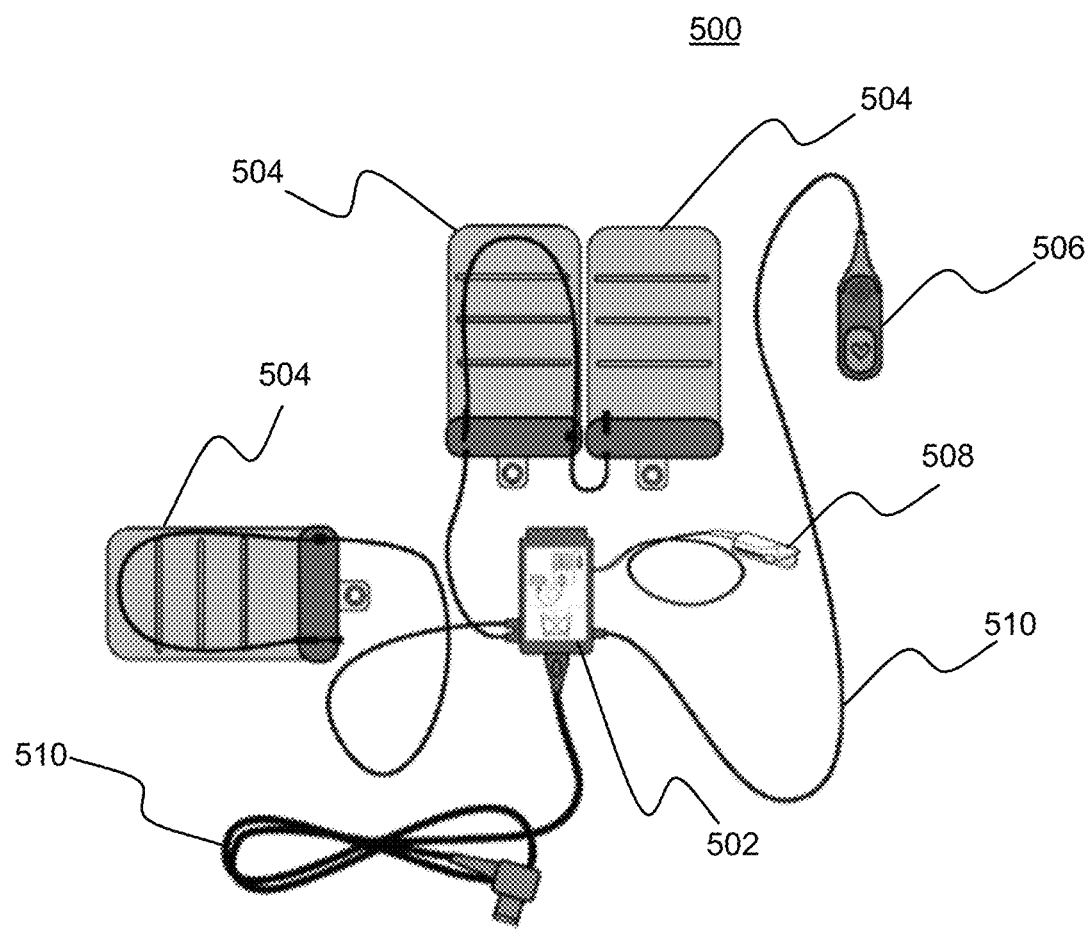
FIG. 5 illustrates a modular system having a pulse oximeter, in accordance with various embodiments.

FIG. 5 illustrates a modular system having a pulse oximeter, in accordance with various embodiments. In FIG. 5, a modular system 500 may include a removable junction module (hub 502), three defibrillator electrodes 504, a user interface (e.g., a button 506), and a pulse oximeter 508. In FIG. 5, the hub 502 may be utilized to receive cables 510 for interconnecting a defibrillator device with ECG sensors (not shown), the pulse oximeter 508, and the button 506, which may include an abort button to stop an impending shock. Additionally, various optional sensors (e.g., impedance sensors, motion sensors, non-invasive blood pressure sensors, etc.) may be communicatively coupled to the hub 502. The hub 502 may include various electronic components such as, but not limited to, circuitry for filtering and/or analog-to-digital conversion of ECG and/or other sensor output signals. The modular system 500 may be included in a support structure as shown in FIG. 6.

Figure 6:
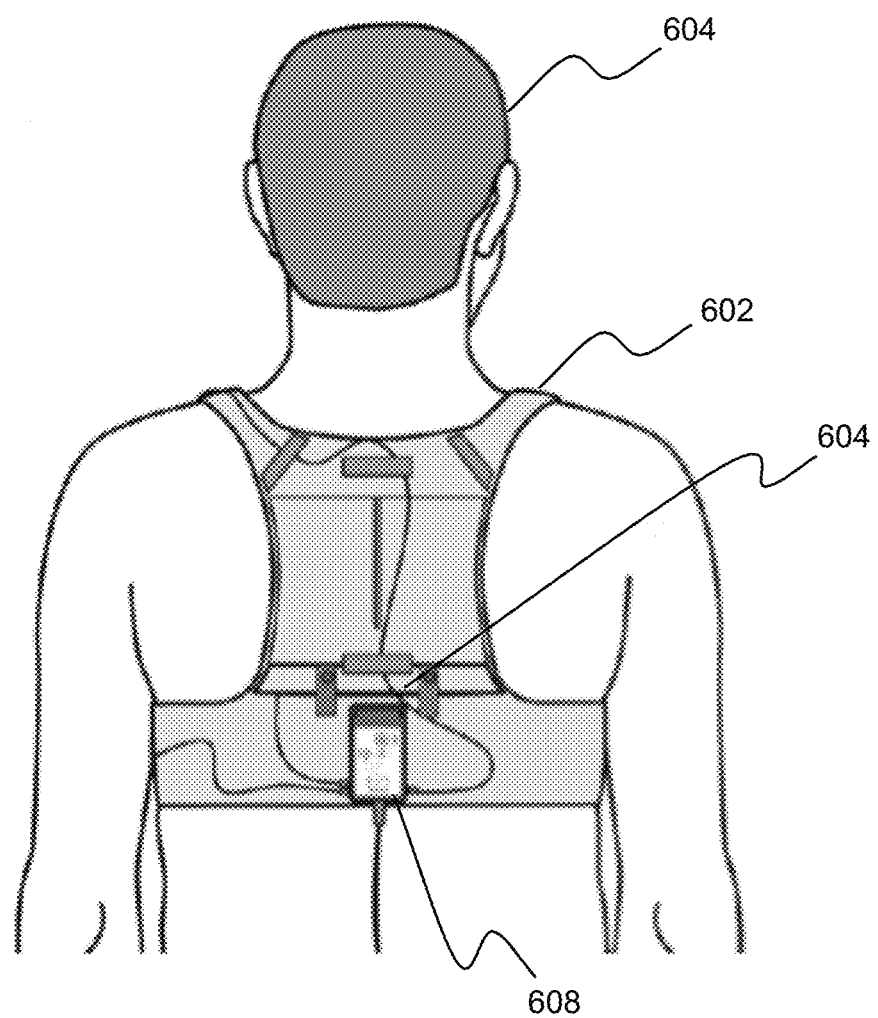
FIG. 6 illustrates a system having a modular system included in a support structure, in accordance with various embodiments.

FIG. 6 illustrates a system having a modular system included in a support structure, in accordance with various embodiments. In FIG. 6, a system 600 may include a support structure (e.g., garment 602) configured to be worn by a person 604. The garment 602 may include an integrated receptacle 606 configured to receive a hub 608 (e.g., the hub 502 shown in FIG. 5). The hub 608 may be held in the receptacle 606 (i.e., attached) by a variety of methods such as, but not limited to snap fitting, latching, etc.

Referring back to FIG. 5 and FIG. 6, the cables 510 for the ECG electrodes 504 and the pulse oximetry 508, which may be located on the front side of the garment 602 may be embedded in the garment 602 (e.g., a belt portion) and not be visible. The cables 510 may be electrically coupled to contacts in the receptacle 604, and accordingly, an electrical coupling may occur when the hub 608 is inserted in the receptacle 604.

Figure 7:
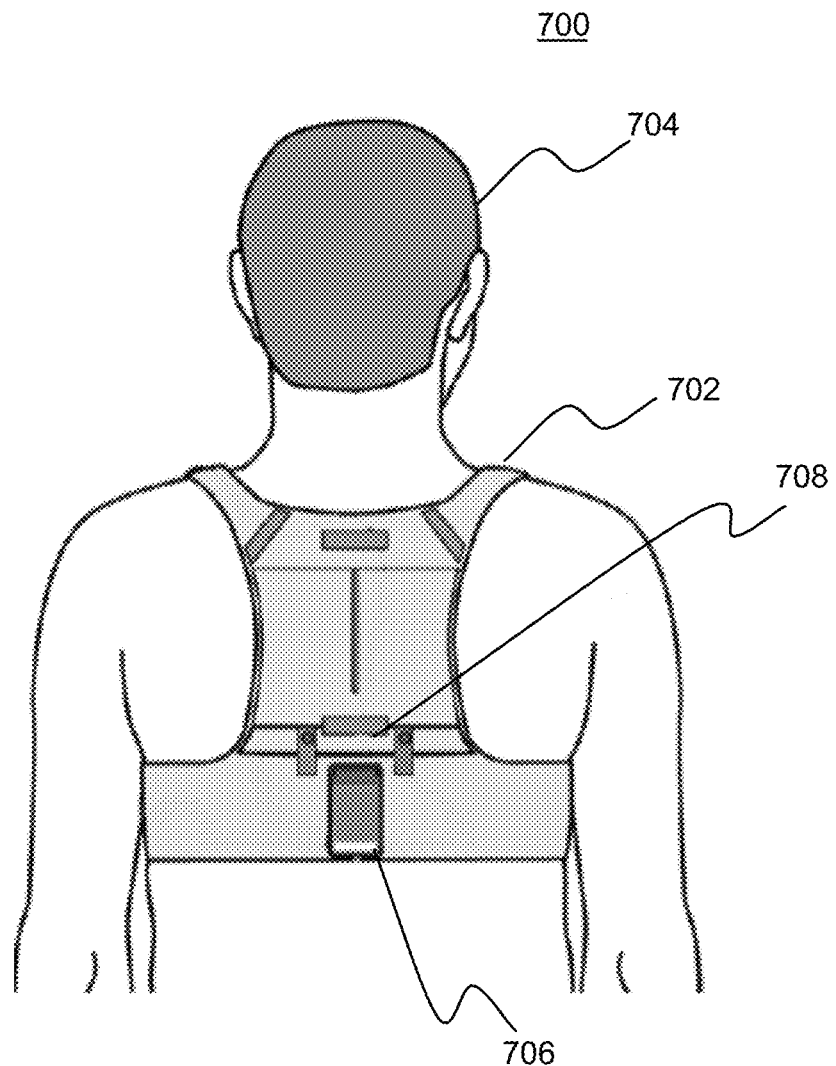
FIG. 7 illustrates a monitoring system, in accordance with various embodiments.

FIG. 7 illustrates a monitoring system, in accordance with various embodiments. In FIG. 7, a monitoring system 700 may include a support structure (e.g., garment 702) configured to be worn by a person 704. The monitoring system 700 may include a monitor module 706 in a receptacle 708. The receptacle 708 may be configured to accommodate a hub (such as the hub 608 shown in FIG. 6). However, in FIG. 7, defibrillator functionality may no longer be needed. Accordingly, the hub 608 may be replaced with the monitor module 706 in the receptacle 708.

In one example, the monitor module 706 may include various electronic components (e.g., a processor and other circuitry) to receive signals from ECG electrodes, a pulse oximeter, and other sensors, which may still attached and/or integrated the garment 702 and/or the person 704. The monitor module 706 may include a storage medium configured to store the various measurements (e.g., ECG and/or blood oxygen saturation level, etc.). That is, the monitor module 706 may be configured to process the various measurements and store the health parameters of the person 704 such as, but not limited to, ECG signals, heart rate, SpO2, respiration rate, step count, etc. As will be described, the health parameters may be personal to the person 706 and may facilitate identifying the person 704.

In some examples, the monitor module 706 may be a smart device type such as, but not limited to, a smart phone type, a tablet type, and/or a smart watch type having health tracking capabilities (e.g., generate health status, trends, etc. and/or statistics related to the person's activity, sleep, wear time, etc.). Accordingly, some of the data may be processed and communicated to a remote server and/or to cloud storage. Alternatively, raw health related data may be communicated to a remote server to be processed and analyzed. This communication may be in a variety of forms such as wired and/or wireless.

It should be appreciated that it is contemplated within the scope of the disclosure that the hub 502 (shown in FIG. 5) may also include various communication capabilities. Accordingly, the hub 502 may include the capabilities of communicating data to a remote server and/or to cloud storage.

The communication capabilities may facilitate remote healthcare services such as, but not limited to, telemedicine. For example, a person's medical personnel may have determined that the person has a high-risk period for VF during which time, the person should be utilizing a WCD. Additionally, there may be a low risk period during which time, the person should be monitored. The WCD system along with a monitor module may be then be provided to the person. The person may utilize the system in the defibrillator configuration of FIG. 6 during the high-risk period. Subsequently, during the low-risk period, the person may reconfigure the system into the monitor configuration of FIG. 7. Once the monitoring period is completed the person may provide the WCD system and the monitor module to the medical personnel or to the vendor of the WCD system and monitor module or to some other designated entity. Alternatively, the information (data) in the WCD system and the monitor module may be communicated (i.e., transmitted) to the medical personnel either via wired and/or wireless communication medium.

In some examples, the WCD system and the monitor module may include storage mediums to store various health related data. The storage medium may be removable and/or non-removeable. The storage medium may be accessed to retrieve the data.

In some examples, the WCD system may be configured to issue prompts to bystanders to place a person's fingertip into/onto the pulse oximeter sensor when the person is determined to be unconscious. For example, some WCD systems include prompting for bystanders to perform CPR on a person, and the pulse oximeter may be utilized to monitor the effectiveness of the CPR and provide CPR feedback to the bystander performing the CPR.

Figure 8:
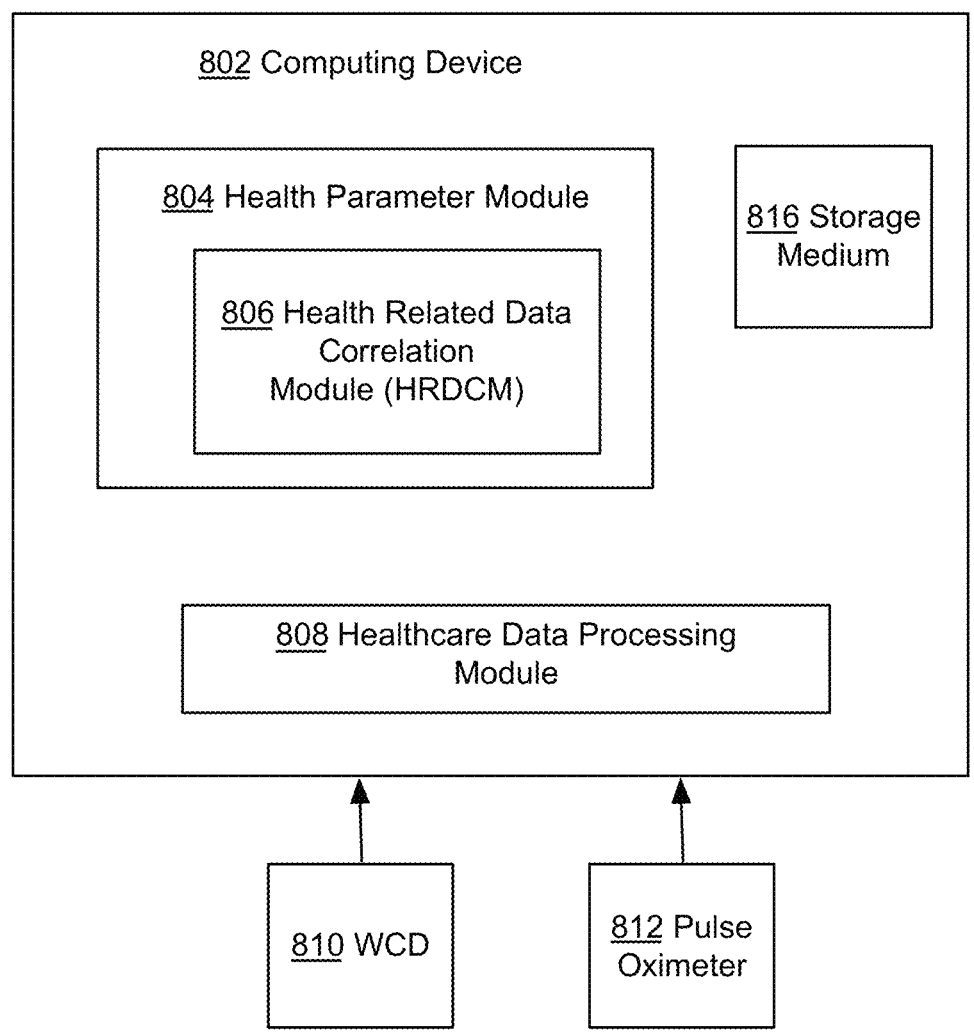
FIG. 8 illustrates a block diagram of an example health parameter identification environment, in accordance with at least some embodiments described herein.

FIG. 8 illustrates a block diagram of an example health parameter identification environment, in accordance with at least some embodiments described herein. In FIG. 8, a health parameter environment 800 may be implemented to determine an identity of a person based, at least in part, on the health parameters of the person. In some examples, the health parameters may be utilized to personalize a WMD for the person.

As depicted, the health parameter environment 800 may include a computing device 802. The computing device 802 may be a variety of computing device upon with health related data may be processed such as, but not limited to, a laptop, a desktop, a server, a tablet computer, a smart phone, or the like.

In FIG. 8, the computing device 802 may include a health parameter module 804, in accordance with various embodiments. The health parameter module 804 may include a health related data correlation module (HRDCM) 806. The HRDCM 806 may be communicatively coupled to a healthcare data processing module 808. The healthcare data processing module 808 may be communicatively coupled to a WCD 810 and to a pulse oximeter 812 (e.g., WCD 100 and pulse oximeter 116 both shown in FIG. 1).

In FIG. 8, the healthcare data processing module 808 may receive an indication of health related data from the WCD 810 (e.g., ECG signals) and receive health related data from the pulse oximeter 812. The data from the WCD 810 may be processed into ECG signals by the healthcare data processing module 808. The data from the WCD 810 may be continuously received via electrodes as a person wears the WCD 810. On the other hand, the data from the pulse oximeter 812 may be received periodically as the person wears the WCD 810. The data from the pulse oximeter 812 may be processed into blood oxygen saturation level and pulse by the healthcare data processing module 808. In accordance with various embodiments, the pulse oximeter 812 may be integrated with a support structure (e.g., garment) having the WCD 810. In this example, the WCD may prompt the person to utilize the pulse oximeter 812 during predetermined times (e.g., 9:00 a.m., 2:00 p.m., and 8:00 p.m.).

The HRDCM 806 may receive the processed data from the healthcare data processing module 808. The HRDCM 806 may correlate the data received from the WCD 810 and the data received from the pulse oximeter 812. This correlated data may be stored in a storage medium 814. The stored correlated data may be utilized by the HRDCM 806 to determine an identity of the person (e.g., biometric determination). For example, the received ECG signal may be correlated to the pulse oximeter measurement.

In one example, as the person continues to wear the WCD 810 and continues to utilize the pulse oximeter 812, the HRDCM 806 may receive numerous data from the two healthcare devices. As more and more data is correlated and stored, the identity of the person may be confirmed.

In another example, the correlated data may facilitate personalization of the healthcare devices (e.g., WCD 810 and pulse oximeter 812). The correlated data may indicate various activities of the person during the day, the week, the month, the year, the years, etc. The indication of the various activities of the person may be utilized by medical personnel to determine how to optimize the use of the medical devices. For example, the person's a high-risk period for VF and low-risk periods for VF may be determined by the medical personnel with the assistance of the correlated data by the HRDCM 806. As a result, the HRDCM 806 may facilitate a personalization of healthcare devices.

It should be appreciated that the components in FIG. 8 may be arranged in a wide variety of manners. For example, the components may be arranged such that they may be separate components, all included as a single component, or any combination thereof, and accordingly, the claimed subject matter is not limited in these respects. Additionally, it should be appreciated that even though the disclosure may have been described utilizing the WCD 810 and the pulse oximeter 812, a wide variety of wearable medical devices may be utilized in combination such as, but not limited to, a respiration monitor with a WCD, and/or pulse oximeter or any combination thereof. The variety of combination of WMDs may be applicable the entire disclosure. Accordingly, the claimed subject matter is not limited in this respect.

It should also be appreciated that it is contemplated within the present disclosure that the health parameter module 804 may be configured to employ methodologies related to determining machine learning such as, but not limited to, methodologies having artificial intelligence/machine learning (AI) capabilities to facilitate at least some of the functionality described herein such as, but not limited to, AI capable processors available from Intel Corporation of Santa Clara, Calif. (e.g., Nervana™ type processors), available from Nvidia Corporation of Santa Clara, Calif. (e.g., Volta™ type processors), available from Apple Company of Cupertino, Calif. (e.g., A11 Bionic™ type processors), available from Huawei Technologies Company of Shenzen, Guangdong, China (e.g., Kirin™ type processors), available from Advanced Micro Devices, Inc. of Sunnyvale, Calif. (e.g., Radeon Instinct™ type processors), available from Samsung of Seoul, South Korea (e.g., Exynos™ type processors), and so forth. Accordingly, the disclosed subject matter is not limited in these respects. The utilization of artificial intelligence may facilitate determining an identity of a person based, at least in part, on stored correlated health related data (e.g., health parameters).

Additionally, any of the above mentioned example processors may facilitate the various processing examples described in the present disclosure. Alternatively, various general purpose processors may facilitate the various processing examples described in the present disclosure such as, but not limited to, iCore series processors available from Intel Corporation of Santa Clara, Calif. (e.g., various generation Core i7, i8, i9, etc. processors). Accordingly, the disclosed subject matter is not limited in these respects.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

As previously mentioned, it should be appreciated after review of this disclosure that the WCD 100 (shown in FIG. 1 and other places in the disclosure) is a simplistic illustration and does not show all of the various components, electronic and non-electronic, of the WCD 100. However, the claimed subject matter disclosed contemplates that there may be numerous components of a WCD that may be integrated into the WCD 100 (i.e., the support structure 102), and accordingly, the claimed subject matter is not limited in this respect. The same may be said for the pulse oximeter 200, 210, and 216 (shown in FIGS. 2A-C and other places in the disclosure) may be a simplistic illustration.

Figure 9:
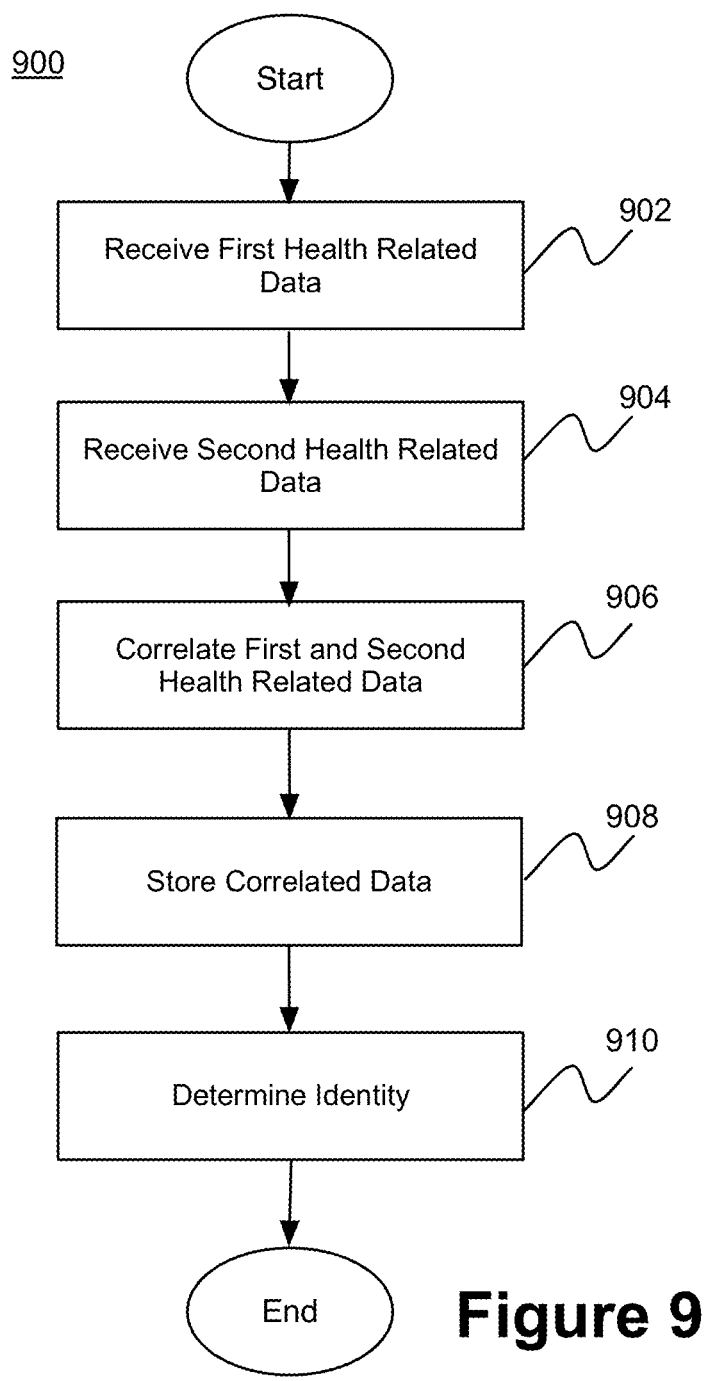
FIG. 9 illustrates an operational flow for determining an identity of a person, arranged in accordance with at least some embodiments described herein.

FIG. 9 illustrates an operational flow for determining an identity of a person, arranged in accordance with at least some embodiments described herein. In some portions of the description, illustrative implementations of the method are described with reference to the elements depicted in FIGS. 1, 5, 7, and 8. However, the described embodiments are not limited to these depictions. More specifically, some components depicted in FIGS. 1, 5, 7, and 8 may be omitted from some implementations of the methods detailed herein. Furthermore, other components not depicted in FIGS. 1, 5, 7, and 8 may be used to implement example methods detailed herein.

Additionally, FIG. 9 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 900 may be employed as part of a WCD communicatively with a pulse oximeter as described herein. Beginning at block 902 ("Receive First Health Related Data"), a WMD such as, but not limited to, a WCD may be included in a support structure. Additionally, a pulse oximeter 116 may be included in the support structure. In this example, a WCD monitor 106 (shown in FIG. 1) may receive an indication of a first health related data from a first healthcare device (e.g., ECG signals from the WCD 106) to be processed by a processor. In some examples, a hub 502, a monitor module 706, and/or a computing device 802 (shown in FIGS. 5, 7, and 8) may be configured to receive the indication of the first health related data.

Continuing from block 902 to 904 ("Receive Second Health Related Data"), at the processor (i.e., any of the examples as described above), an indication of a second health related data from a second healthcare device may be received. For example, from the pulse oximeter 116, which may be included in the support structure 102 (shown in FIG. 1), in accordance with various embodiments.

Continuing from block 904 to 906 ("Correlate First and Second Health Related Data"), the processor may correlate the indication of the first health related data with the second health related data (e.g., ECG signals correlated with pulse oximeter measurements).

Continuing from block 906 to 908 ("Store Correlated Data"), the correlated indications may be stored in a storage medium (e.g., storage medium 816 shown in FIG. 8).

Continuing from block 908 to 910 ("Determine Identity"), the processor may determine an identity of a person based, at least in part, on the stored correlated indications. For example, the ECG signals correlated with pulse oximeter measurements may correspond to identification of various activities of a person, which in turn may facilitate identification of the person, in accordance with various embodiments.

In general, the operational flow described with respect to FIG. 9 may be implemented as a computer program product, executable on any suitable computing system or the like. For example, a computer program product for determining an identity of a person based, at least in part, on stored correlated indications. Example computer program product may be described with respect to FIG. 10 and elsewhere herein.

FIG. 10 illustrates an example computer program product arranged, in accordance with at least some embodiments described herein. Computer program product 1000 may include machine readable non-transitory medium having stored therein instructions that, when executed, cause the machine to an identity of a person base, at least in part, on stored correlated health parameters according to the processes and methods discussed herein. Computer program product 1000 may include a signal bearing medium 1002. Signal bearing medium 1002 may include one or more machine-readable instructions 1004, which, when executed by one or more processors, may operatively enable a computing device to provide the functionality described herein. In various examples, some or all of the machine-readable instructions may be used by the devices discussed herein.

In some examples, the machine readable instructions 1004 when executed by one or more processors may receive, at the processor, an indication of a first health related data from a first healthcare device. In some examples, the machine readable instructions 1004 when executed may receive, at the processor, an indication of a second health related data from a second healthcare device. In some examples, the machine readable instructions 1004 when executed may correlate, by the processor, the indication of the first health related data with the second health related data. In some examples, the machine readable instructions 1004 when execute may store, at a storage medium, the correlated indications of the first health related data and the second health related data. In some examples, the machine readable instructions 1004 when executed may determine, by the processor, an identity of a person based, at least in part, on the stored correlated indications.

In some implementations, signal bearing medium 1002 may encompass a computer-readable medium 1006, such as, but not limited to, a hard disk drive, a Compact Disc (CD), a Digital Versatile Disk (DVD), a digital tape, memory, etc. In some implementations, the signal bearing medium 1002 may encompass a recordable medium 1008, such as, but not limited to, memory, read/write (R/W) CDs, R/W DVDs, etc. In some implementations, the signal bearing medium 1002 may encompass a communications medium 1010, such as, but not limited to, a digital and/or an analog communication medium (e.g., a fiber optic cable, a waveguide, a wired communication link, a wireless communication link, etc.). In some examples, the signal bearing medium 502 may encompass a machine readable non-transitory medium.

In general, the methods described with respect to FIG. 9 and elsewhere herein may be implemented in any suitable computing system and/or WMD. Example systems may be described with respect to FIG. 12 and elsewhere herein. In general, the system may be configured to determine an identity of a person.

Figure 11:
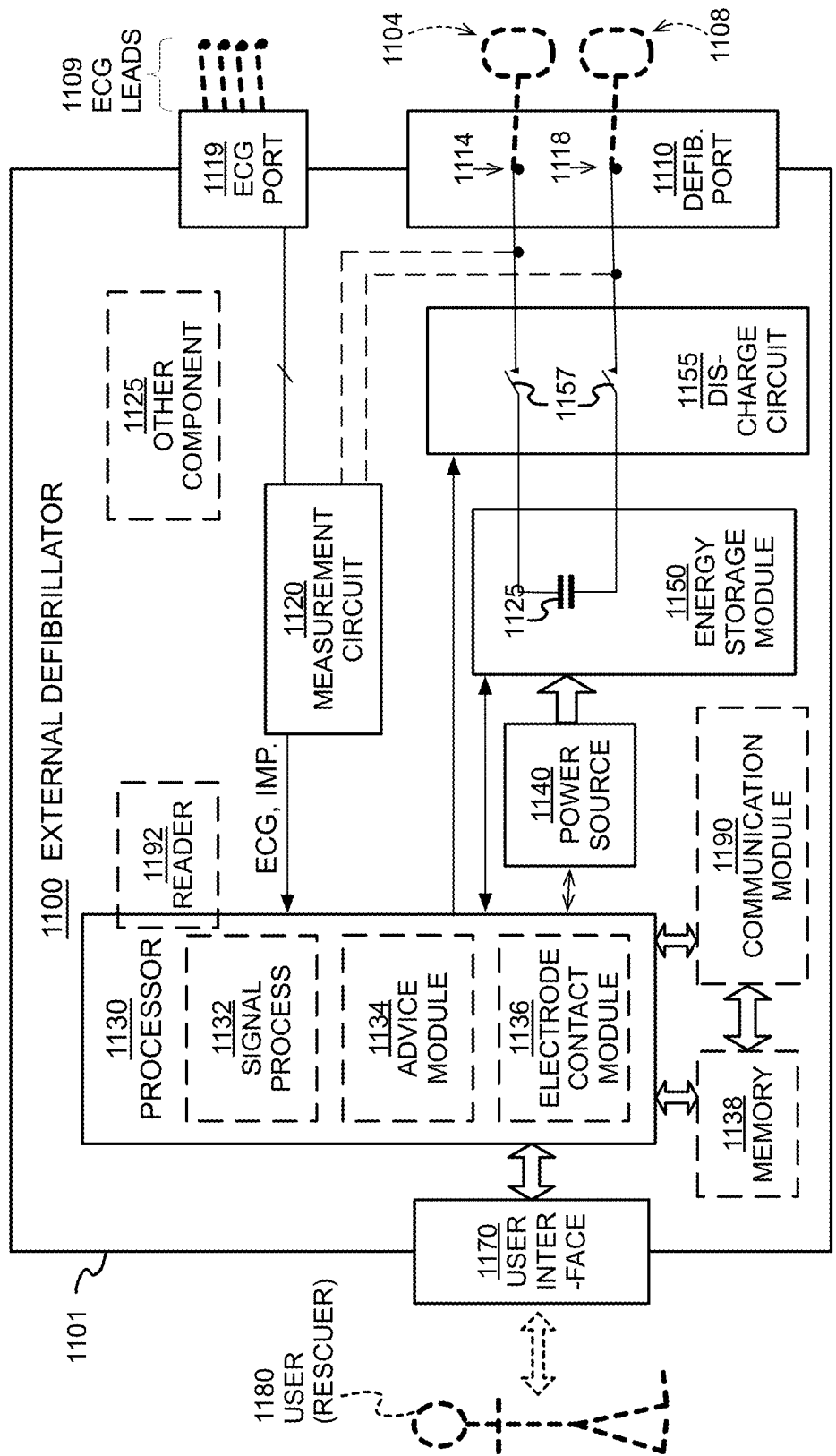
FIG. 11 is a block diagram illustrating components of a defibrillator device, which may be used with various embodiments.

FIG. 11 is a block diagram illustrating components of a defibrillator device, which may be used with various embodiments. These components may be, for example, components of a WCD 100, 300, 308, 502, 608, and 810 (shown in FIGS. 1, 3A-B, 5, 6, and 8).

The defibrillator device 1100 may be some of the above examples of an one or more modules for the WCD (e.g., WCD monitor 106 shown in FIG. 1) intended for use by a user 1180 (e.g., a wearer or person 104, 302, 310, 604, and 704 shown in FIGS. 1, 3A-B, 6, and 7). The defibrillator device 1100 may typically include a defibrillation port 1110, such as a socket in housing 1101. The defibrillation port 1110 may include nodes 1114 and 1118. One or more electrodes 1104 and 1108, which may be plugged into the defibrillation port 1110, so as to make electrical contact with nodes 1114 and 1118, respectively. It may also be possible that the electrodes 1104 and 1108 may be connected continuously to the defibrillation port 1110, etc. Either way, the defibrillation port 1110 may be used for guiding via the electrodes 1104 and 1108 to a person 1104 an electrical charge that may have been stored in the defibrillator device 1100, as described herein.

The defibrillator device 1100 may also have an ECG port 1119 in the housing 1101, for receiving ECG cables 1109. The ECG cables 1109 may facilitate sensing of an ECG signal (e.g., a 12-lead signal or from a different number of lead signals). Moreover, a defibrillator-monitor could have additional ports (not shown), and the other component 1125 may be configured to filter the ECG signal (e.g., application of at least one filter to the signal to help facilitate removal of artifacts such as, but not limited to, chest compression due to chest compressions being delivered to the person).

The defibrillator 1100 also may include a measurement circuit 1120. The measurement circuit 1120 may receive physiological signals from the ECG port 1119, and also from other ports, if provided. The circuit 1120 may render detected physiological signals and their corresponding information. The information may be in the form of data, or other signals, etc.

If the defibrillator 1100 is configured as a WCD type device as described herein, ECG port 1119 may not be present. The measurement circuit 1120 may obtain physiological signals through the nodes 1114 and 1118 instead, when the electrodes 1104 and 1108 are attached to the person 1104. In these cases, a person's ECG signal may be detected as a voltage difference between the electrodes 1104 and 1108. Additionally, the impedance between the electrodes 1104 and 1108 may be detected, among other things, whether the electrodes 1104 and 1108 have been inadvertently disconnected from the person.

The defibrillator 1100 may also include a processor 1130. The processor 1130 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 1130 may include a number of modules. One example module may be a detection module 1132, which may detect outputs from the measurement circuit 1120. The detection module 1132 may include a VF detector. Accordingly, the person's detected ECG may be utilized to help determine whether the person is experiencing ventricular fibrillation (VF).

In another example module may be an advice module 1134, which may provide advice based, at least in part, on outputs of detection module 1132. The advice module 1134 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user, and prompt them to do it. In other examples, the defibrillator device may execute the advice by administering the shock. If the advice is to administer CPR, the defibrillator 1100 may further issue prompts for administrating CPR, and so forth.

The processor 1130 may include additional modules, such as module 1136 for various other functions. Additionally, if other component 1125 is provided, it may be operated in part by processor 1130, etc.

In an example, the defibrillator device 1100 may include a memory 1138, which may work together with the processor 1130. The memory 1138 may be implemented in a wide variety of manners. For example, the memory 1138 may be implemented such as, but not limited to, nonvolatile memories (NVM), read-only memories (ROM), random access memories (RAM), and so forth or any combination thereof. The memory 1138 may can include programs for the processor 1130, and so on. The programs may include operational programs execution by the processor 1130 and may also include protocols and methodologies that decisions may be made by advice module 1134. Additionally, the memory 1138 may store various prompts for the user 1180, etc. Moreover, the memory 1138 may store a wide variety of information (i.e., data) such as, but not limited to information regarding the person.

The defibrillator 1100 may also include a power source 1140. In order to facilitate portability of defibrillator device 1100, the power source 1140 may include a battery type device. A battery type device may be implemented as a battery pack, which may be rechargeable or not be rechargeable. At times, a combination of rechargeable and non-rechargeable battery packs may be utilized. Examples of power source 1140 may include AC power override, where AC power may be available, and so on. In some examples, the processor 1130 may control the power source 1140.

Additionally, the defibrillator device 1100 may include an energy storage module 1150. The energy storage module 1150 may be configured to store some electrical energy (e.g., when preparing for sudden discharge to administer a shock). The energy storage module 1150 may be charged from the power source 1140 to an appropriate level of energy, as may be controlled by the processor 1130. In some implementations, the energy storage module 1150 may include one or more capacitors 1152, and the like.

The defibrillator 1100 may include a discharge circuit 1155. The discharge circuit 1155 may be controlled to facilitate discharging of the energy stored in energy storage module 1150 to the nodes 1114 and 1118, and also to electrodes 1104 and 1108. The discharge circuit 1155 may include one or more switches 1157. The one or more switches 1157 may be configured in a number of manners such as, but not limited to, an H-bridge, and so forth.

The defibrillator device 1100 may further include a user interface 1170 for the user 1180. The user interface 1170 may be implemented in a variety of manners. For example, the user interface 1170 may include a display screen capable of displaying what is detected and measured, provide visual feedback to the user 1180 for their resuscitation attempts, and so forth. The user interface 1170 may also include an audio output such as, but not limited to, a speaker to issue audio prompts, etc. The user interface 1170 may additionally include various control devices such as, but not limited to, pushbuttons, touch display, and so forth. Additionally, the discharge circuit 1155 may be controlled by the processor 1130 or directly by the user 1180 via the user interface 1170, and so forth.

Additionally, the defibrillator device 1100 may include other components. For example, a communication module 1190 may be provided for communicating with other machines and/or the electrodes. Such communication may be performed wirelessly, or via wire, or by infrared communication, and so forth. Accordingly, information may be communicated, such as person data, incident information, therapy attempted, CPR performance, ECG information, and so forth.

Figure 12:
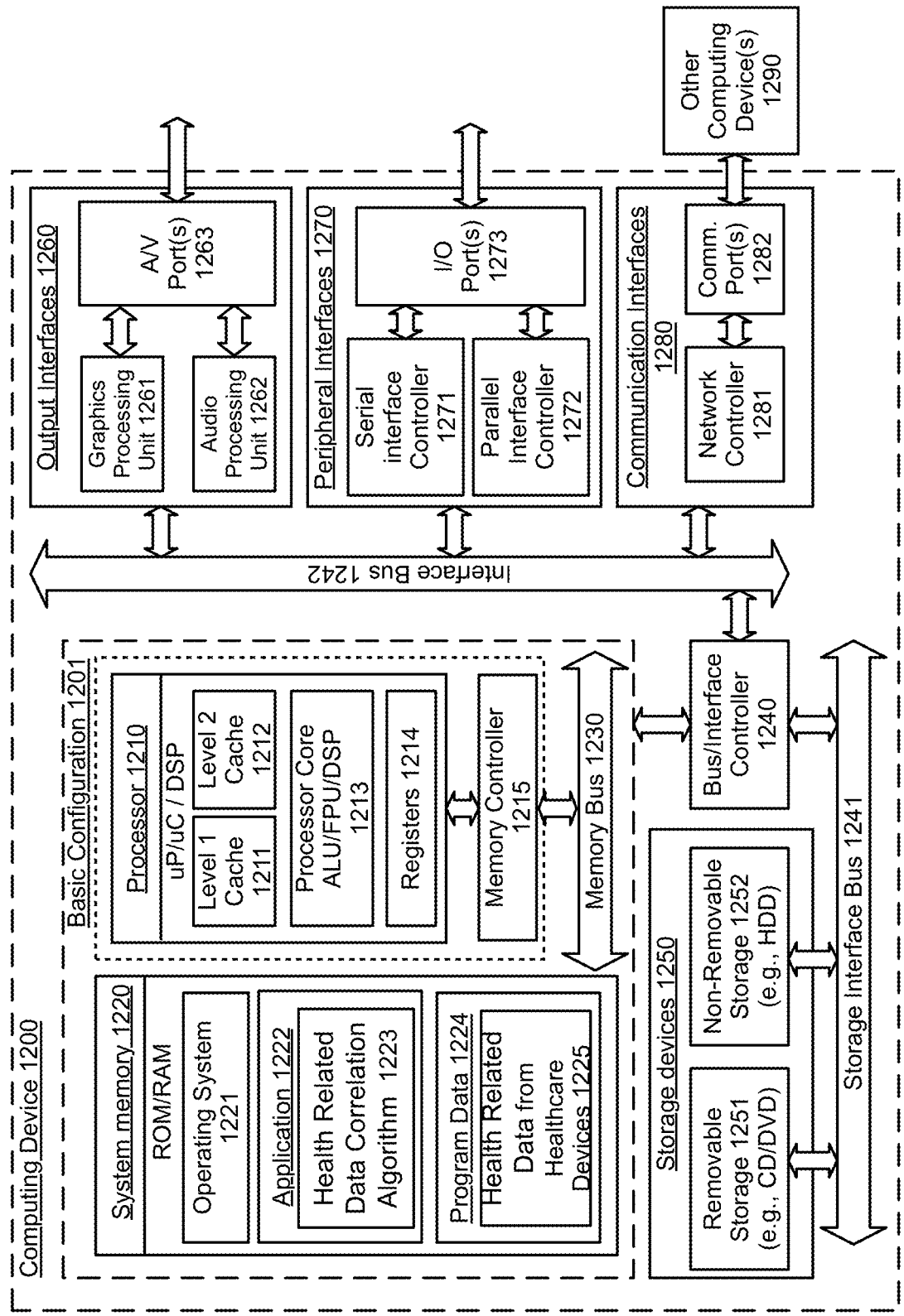
FIG. 12 is a block diagram illustrating an example computing device, such as might be embodied by a person skilled in the art, which is arranged in accordance with at least some embodiments of the present disclosure

FIG. 12 is a block diagram illustrating an example computing device 1200, such as might be embodied by a person skilled in the art, which is arranged in accordance with at least some embodiments of the present disclosure. In one example configuration, computing device 1200 may include one or more processors 1210 and system memory 1220. A memory bus 1230 may be used for communicating between the processor 1210 and the system memory 1220.

Depending on the desired configuration, processor 1210 may be of any type including but not limited to a microprocessor (μP), a microcontroller (μC), a digital signal processor (DSP), or any combination thereof. Processor 1210 may include one or more levels of caching, such as a level one cache 1211 and a level two cache 1212, a processor core 1213, and registers 1214. The processor core 1213 may include an arithmetic logic unit (ALU), a floating point unit (FPU), a digital signal processing core (DSP Core), or any combination thereof. A memory controller 1215 may also be used with the processor 1210, or in some implementations the memory controller 1215 may be an internal part of the processor 1210.

Depending on the desired configuration, the system memory 1220 may be of any type including but not limited to volatile memory (such as RAM), non-volatile memory (such as ROM, flash memory, etc.) or any combination thereof. System memory 1220 may include an operating system 1221, one or more applications 1222, and program data 1224. Application 1222 may health related data correlation algorithm 1223 (e.g., HRDCM) that is arranged to perform the functions as described herein including the functional blocks and/or actions described. Program Data 1224 may include, among other information described healthcare data 1225 from two or more healthcare devices for use with health related data correlation algorithm 1223. In some example embodiments, application 1222 may be arranged to operate with program data 1224 on an operating system 1221 such that implementations of defibrillator and pulse oximeters provided as described herein. For example, apparatus described in the present disclosure may comprise all or a portion of computing device 1200 and be capable of performing all or a portion of application 1222 such that determining an identify of a person as described herein. This described basic configuration is illustrated in FIG. 12 by those components within dashed line 1201.

Computing device 1200 may have additional features or functionality, and additional interfaces to facilitate communications between the basic configuration 1201 and any required devices and interfaces. For example, a bus/interface controller 1240 may be used to facilitate communications between the basic configuration 1201 and one or more data storage devices 1250 via a storage interface bus 1241. The data storage devices 1250 may be removable storage devices 1251, non-removable storage devices 1252, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable, and non-removable media implemented in any method or technology for storage of information, such as computer readable instructions, data structures, program modules, or other data.

System memory 1220, removable storage 1251 and non-removable storage 1252 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 1200. Any such computer storage media may be part of device 1200.

Computing device 1200 may also include an interface bus 1242 for facilitating communication from various interface devices (e.g., output interfaces, peripheral interfaces, and communication interfaces) to the basic configuration 1201 via the bus/interface controller 1240. Example output interfaces 1260 may include a graphics processing unit 1261 and an audio processing unit 1262, which may be configured to communicate to various external devices such as a display or speakers via one or more A/V ports 1263. Example peripheral interfaces 1260 may include a serial interface controller 1271 or a parallel interface controller 1272, which may be configured to communicate with external devices such as input devices (e.g., keyboard, mouse, pen, voice input device, touch input device, etc.) or other peripheral devices (e.g., printer, scanner, etc.) via one or more I/O ports 1273. An example communication interface 1280 includes a network controller 1281, which may be arranged to facilitate communications with one or more other computing devices 1290 over a network communication via one or more communication ports 1282. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 1200 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 1200 may also be implemented as a personal computer including both laptop computer and non-laptop computer configurations. In addition, computing device 1200 may be implemented as part of a wireless base station or other wireless system or device.

It should be appreciated after review of this disclosure that it is contemplated within the scope and spirit of the present disclosure that the claimed subject matter may include a wide variety of healthcare devices. Accordingly, the claimed subject matter is not limited in these respects.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to the particular examples disclosed, but that such claimed subject matter also may include all implementations falling within the scope of the appended claims, and equivalents thereof.

What is claimed:

1. An apparatus comprising:
a support structure, the support structure configured to be worn by a person;
a plurality of electrodes coupled to the support structure, the plurality of electrodes configured to receive electrocardiogram (ECG) signals from the person;
a blood oxygen saturation level device included in the support structure;
a wearable cardioverter defibrillator (WCD) device communicatively coupled to the plurality of electrodes and the blood oxygen saturation level device,
the WCD device configured to:
detect a cardiac event based on the ECG signals, the cardiac event being at least one of ventricular fibrillation (VF) or ventricular tachycardia (VT),
prepare to deliver an electrical shock to the person,
prompt the person to utilize the blood oxygen saturation level device to obtain a blood oxygen measurement in response to the cardiac based event being detected,
abort delivery of electrical shock by the WCD device in response to receiving the blood oxygen measurement; and
deliver the electrical shock when the blood oxygen measurements is not received within a predetermined period.

2. The apparatus of claim 1, wherein the support structure comprises a garment.

3. The apparatus of claim 1, wherein the blood oxygen saturation level device comprises a pulse oximeter sensor.

4. The apparatus of claim 1, wherein the blood oxygen saturation level device is configured to receive power from the WCD.

5. The apparatus of claim 1, wherein the blood oxygen saturation level device comprises a cover and a sensor recessed into the support structure.

6. The apparatus of claim 5, wherein the cover is configured to activate the sensor when the cover is opened.

7. The apparatus of claim 5, wherein the cover is configured to detect a presence of a finger placed on the sensor.

8. The apparatus of claim 1, wherein the blood oxygen saturation level device is disposed in a pocket integrated with the support structure, the pocket configured to accommodate a finger.

9. The apparatus of claim 8, wherein the pocket is further configured to accommodate a sensor.

10. The apparatus of claim 9, wherein the sensor is configured to detect a presence of the finger placed on the sensor.

11. The apparatus of claim 1, wherein the blood oxygen saturation level device is configured to be attachable to and detachable from the support structure.

12. The apparatus of claim 11, wherein the blood oxygen saturation level device includes hook and loop fasteners.

13. The apparatus of claim 11, wherein the blood oxygen saturation level device includes snap fasteners.

14. The apparatus of claim 11, wherein the blood oxygen saturation level device includes magnets.

15. The apparatus of claim 1, wherein the WCD and the blood oxygen saturation level device are configured to be modular.

16. The apparatus of claim 1, wherein the plurality of electrodes comprises the plurality of electrodes included in the support structure.

17. The apparatus of claim 1, wherein the blood oxygen saturation level device comprises the blood oxygen saturation level device included in the support structure.

18. The apparatus of claim 1, wherein the WCD device comprises an abort button configured to cause the WCD device to stop an impending electrical shock when actuated, and the WCD device is configured to deliver the electrical shock when the blood oxygen measurements is not received within a predetermined period and the abort button is not actuated.

19. A method for identifying a person by a wearable cardioverter defibrillator (WCD), the method comprising:
receiving, at a processor included in the WCD, an indication of a first health related data from a first healthcare device;
receiving, at the processor included in the WCD, an indication of a second health related data from a second healthcare device;
correlating, by the processor included in the WCD, the indication of the first health related data with the second health related data;
storing, at a storage medium included in the WCD, the correlated indications of the first health related data and the second health related data; and
determining, by the processor included in the WCD, an identity of the person based, at least in part, on the stored correlated indications.

20. The method of claim 19 further comprising:
receiving, at the processor, a plurality of subsequent indications of the first health related data from the first healthcare device;
receiving, at the processor, a plurality of subsequent indications of the second health related data from the second healthcare device;
correlating, by the processor, the plurality of subsequent indications of the first health related data with the plurality of subsequent indications of the second health related data;
storing, at the storage medium, the correlated plurality of subsequent indications; and
confirming, by the processor, the identity of the person based, at least in part, on the stored correlated plurality of subsequent indications.

* * * * *